United States Patent
Zholudev et al.

(10) Patent No.: US 11,120,362 B2
(45) Date of Patent: Sep. 14, 2021

(54) IDENTIFYING A PRODUCT IN A DOCUMENT

(71) Applicants: Viacheslav Zholudev, Berlin (DE); Darren Alvares, Berlin (DE); Niall Kelly, Berlin (DE); Tilo Mathes, Berlin (DE); Axel Tölke, Berlin (DE); Vincenz Priesnitz, Berlin (DE); Thoralf Klein, Berlin (DE)

(72) Inventors: Viacheslav Zholudev, Berlin (DE); Darren Alvares, Berlin (DE); Niall Kelly, Berlin (DE); Tilo Mathes, Berlin (DE); Axel Tölke, Berlin (DE); Vincenz Priesnitz, Berlin (DE); Thoralf Klein, Berlin (DE)

(73) Assignee: ResearchGate GmbH, Berlin (DE)

( * ) Notice: Subject to any disclaimer, the term of this patent is extended or adjusted under 35 U.S.C. 154(b) by 975 days.

(21) Appl. No.: 15/635,655

(22) Filed: Jun. 28, 2017

(65) Prior Publication Data

US 2019/0005405 A1    Jan. 3, 2019

(51) Int. Cl.
    *G06N 20/00*     (2019.01)
    *G16H 70/40*     (2018.01)

(52) U.S. Cl.
    CPC ............ *G06N 20/00* (2019.01); *G16H 70/40* (2018.01)

(58) Field of Classification Search
    CPC ............................. G06N 20/00; G16H 70/40
    See application file for complete search history.

(56) References Cited

U.S. PATENT DOCUMENTS

| | | | |
|---|---|---|---|
| 9,674,259 B1 * | 6/2017 | Venkatasubramanian | H04L 67/02 |
| 2008/0262923 A1 | 10/2008 | Farmer et al. | |
| 2014/0095463 A1 | 4/2014 | Pappas | |
| 2015/0331936 A1 * | 11/2015 | Alqadah | G06F 16/313 707/739 |

(Continued)

OTHER PUBLICATIONS

Krauthammer et al., "Term identification in the biomedical literature", 2004, Journal of Biomedical Informatics 34, pp. 512-526 (Year: 2004).*

(Continued)

*Primary Examiner* — Kamran Afshar
*Assistant Examiner* — Brent Johnston Hoover
(74) *Attorney, Agent, or Firm* — Schwegman Lundberg & Woessner, P.A.

(57) ABSTRACT

Aspects of the present disclosure relate to identifying a product in a document. A computing machine accesses a product mention in a scientific or research-related text, the product mention including one or more attribute values for a plurality of attributes, each attribute being associated with either a single attribute value or no attribute value. The computing machine determines that the attribute values of the product mention correspond to two or more candidate product matches in a product directory. The computing machine identifies, based at least in part on stored data related to the scientific or research-related text, a product match from among the candidate product matches, the product match corresponding to the product mention in the scientific or research-related text. The computing machine provides an output of the product match for storage in conjunction with the product mention in the scientific or research-related text.

25 Claims, 8 Drawing Sheets

(56) References Cited

U.S. PATENT DOCUMENTS

2016/0180437 A1* 6/2016 Boston .................... G06F 40/30
                                                     705/26.7
2016/0232155 A1* 8/2016 Allen ............... G06Q 10/06316
2018/0060041 A1   3/2018 Williams et al.
2018/0336182 A1* 11/2018 Lachmi ............... G06F 16/9535
2019/0005404 A1   1/2019 Zholudev et al.

OTHER PUBLICATIONS

"U.S. Appl. No. 15/635,607, Non Final Office Action dated Aug. 18, 2020", 33 pgs.
"U.S. Appl. No. 15/635,607, Examiner Interview Summary dated Oct. 14, 2020", 4 pgs.
"U.S. Appl. No. 15/635,607, Response filed Oct. 7, 2020 to Non Final Office Action dated Aug. 18, 2020", 13 pgs.
"U.S. Appl. No. 15/635,607, Examiner Interview Summary dated Jan. 29, 2021", 2 pgs.
"U.S. Appl. No. 15/635,607, Final Office Action dated Jan. 8, 2021", 44 pgs.
"U.S. Appl. No. 15/635,607, Notice of Allowance dated Mar. 3, 2021", 16 pgs.
"U.S. Appl. No. 15/635,607, Response filed Feb. 18, 2021 to Final Office Action dated Jan. 8, 2021", 14 pgs.

* cited by examiner

IDENTIFYING A PRODUCT IN A DOCUMENT

RELATED APPLICATION

This application relates to U.S. patent application Ser. No. 15/635,607, titled "IDENTIFYING A PRODUCT IN A DOCUMENT," and being filed concurrently herewith, the entire content of which is incorporated herein by reference.

TECHNICAL FIELD

The subject matter disclosed herein relates to data processing. In particular, example embodiments may relate to identifying a product in a document.

BACKGROUND

A researcher reviewing a document that includes scientific or research-related text may wish to learn about the products (e.g., antibodies, chemicals, or machinery) that was used in conducting the research for creating the document. However, accessing information about those products may be challenging.

BRIEF DESCRIPTION OF THE DRAWINGS

Various ones of the appended drawings merely illustrate example embodiments of the present inventive subject matter and cannot be considered as limiting its scope.

DETAILED DESCRIPTION

Reference will now be made in detail to specific example embodiments for carrying out the inventive subject matter. Examples of these specific embodiments are illustrated in the accompanying drawings, and specific details are set forth in the following description in order to provide a thorough understanding of the subject matter. It will be understood that these examples are not intended to limit the scope of the claims to the illustrated embodiments. On the contrary, they are intended to cover such alternatives, modifications, and equivalents as may be included within the scope of the disclosure. Examples merely typify possible variations. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

As noted above, techniques for identifying a product in a document including scientific or research-related text, and providing information about the product, may be desirable. Some aspects of the subject technology are directed to such techniques. According to some implementations, a server (or another computing machine) receives an input including multiple documents (e.g., research papers or other documents including scientific or research-related text) with identified (e.g., by a human or another machine) commercial products within the documents. The server is trained, using the input, to compute a score indicative of a probability that tokens within each document correspond to a commercial product. Each token includes a part of the text that logically comprises a unit of information. Commercial products are identified by one or more of: a name, a catalog identification number, a manufacturer, and a location of the manufacturer.

After the initial training, the sever accesses a document (which might not be from the training set) that includes scientific or research-related text. The server divides the document into multiple tokens. The server computes, for each token, a score/probability that the token corresponds to a commercial product. If the score/probability exceeds a threshold score/probability (e.g., 95% or 97%), the server provides an output representing that the token corresponds to the commercial product. As used herein, a score may include a probability or another type of score may be used. The score may be equal to or proportional to the probability that the token corresponds to the commercial product. The score may be some monotonic function of that probability.

Figure 1:
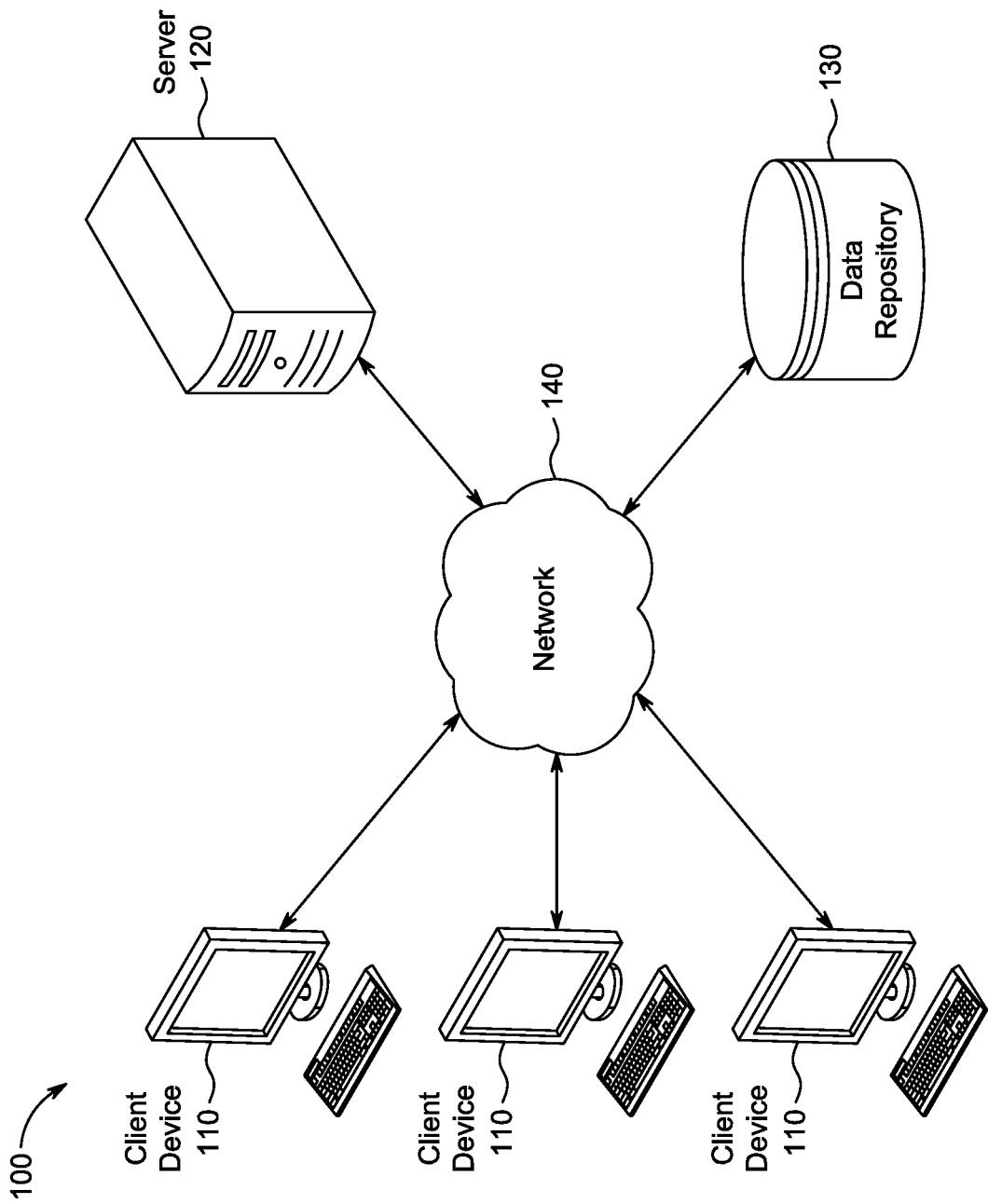
FIG. 1 is a diagram of an example system in identifying a product in a document may be implemented, according to some embodiments.

FIG. 1 is a diagram of an example system 100 in which identifying a product in a document may be implemented. As shown, the system 100 includes client device(s) 110, a server 120, and a data repository 130 connected to one another via a network 140. The network 140 may include one or more of the Internet, an intranet, a local area network, a wide area network (WAN), a cellular network, a WiFi network, a virtual private network (VPN), a public network, a wired network, a wireless network, etc. Aspects of the subject technology are implemented at the server 120, which accesses and stores data at the data repository 130, and provides output via a graphical user interface (GUI) at display unit(s) of the client device(s) 110.

The client device(s) 110 may include one or more of a laptop computer, a desktop computer, a mobile phone, a tablet computer, a personal digital assistant (PDA), a digital music player, a smart watch, and the like. The client device 110 may include an application (or multiple applications), such as a web browser or a special purpose application, for communicating with the server 120 and the data repository 130. Using the application, a user of the client device 110 may access and interface with documents and information about products stored in the data repository 130 using the techniques described herein. While three client devices 110 are illustrated in FIG. 1, the subject technology may be implemented with any number of client device(s) 110. The client device 110 may provide for display of information related to document(s) or product(s), for example, as shown in FIGS. 3-6.

The data repository 130 stores information about documents and information about products. The information about products may include a table (or other data structure) of cataloged products. The data in the data repository 130 is accessible to the server 120. According to one example, the data repository 130 stores documents that are used for training the server 120 to identify products and documents from which the server 120 identifies products after training. The data repository 130 is used for extraction of products and related features, validation of products based on features (e.g., comparison to products in a manufacturer's catalog based on the manufacturer's name), and for matching a product identified in a document to a product in a manufacturer's catalog. Valid products that are either matched or unmatched are stored in a data model. An example of a cataloged products data model is shown in Table 1. The data repository 130 may be implemented as a database or any other data storage unit.

TABLE 1

Cataloged Products Data Model

ProductID
Long categoryId; // Denoting product type, e.g., antibodies, microscopes
String name;
String manufacturer;
String catalogNumber;
List features;
// e.g., antibodies: {host => "mouse", target_species => "human", target_antigen => comment}
Date creationDate;
Date lastModifiedDate;

The server 120 stores data or instructions. The server 120 is configured to identify a product in a document. The product may be a cataloged product from the data repository 130, and the document may be stored in the data repository 130. More details of the operation of the server 120 are provided throughout this document, for example, in conjunction with FIG. 2.

In the implementation illustrated in FIG. 1, the system 100 includes a single data repository 130 and a single server 120. However, the subject technology may be implemented with multiple data repositories or multiple servers. Furthermore, as shown in FIG. 1, a single network 140 connects the client device(s) 110, the server 120, and the data repository 130. However, the subject technology may be implemented using multiple networks to connect the machines. Additionally, while the server 120 and the data repository 130 are illustrated as being distinct machines, in some examples, a single machine functions as both the server 120 and the data repository 130. Also, one or more of the client device(s), the server 120, and the data repository 130 may be implemented as a virtual machine, rather than as a physical machine as shown in FIG. 1.

A machine (e.g., the server 120 or the client device(s) 110) may be configured to carry out functions by having the functions stored in software in a memory that is accessible by the processor(s) of the machine. Alternatively, the machine may be configured to carry out the functions by having the functions hard-coded into the hardware of the processors. In some examples, the machine is configured to carry out the functions using a combination of software and hardware.

Figure 2:
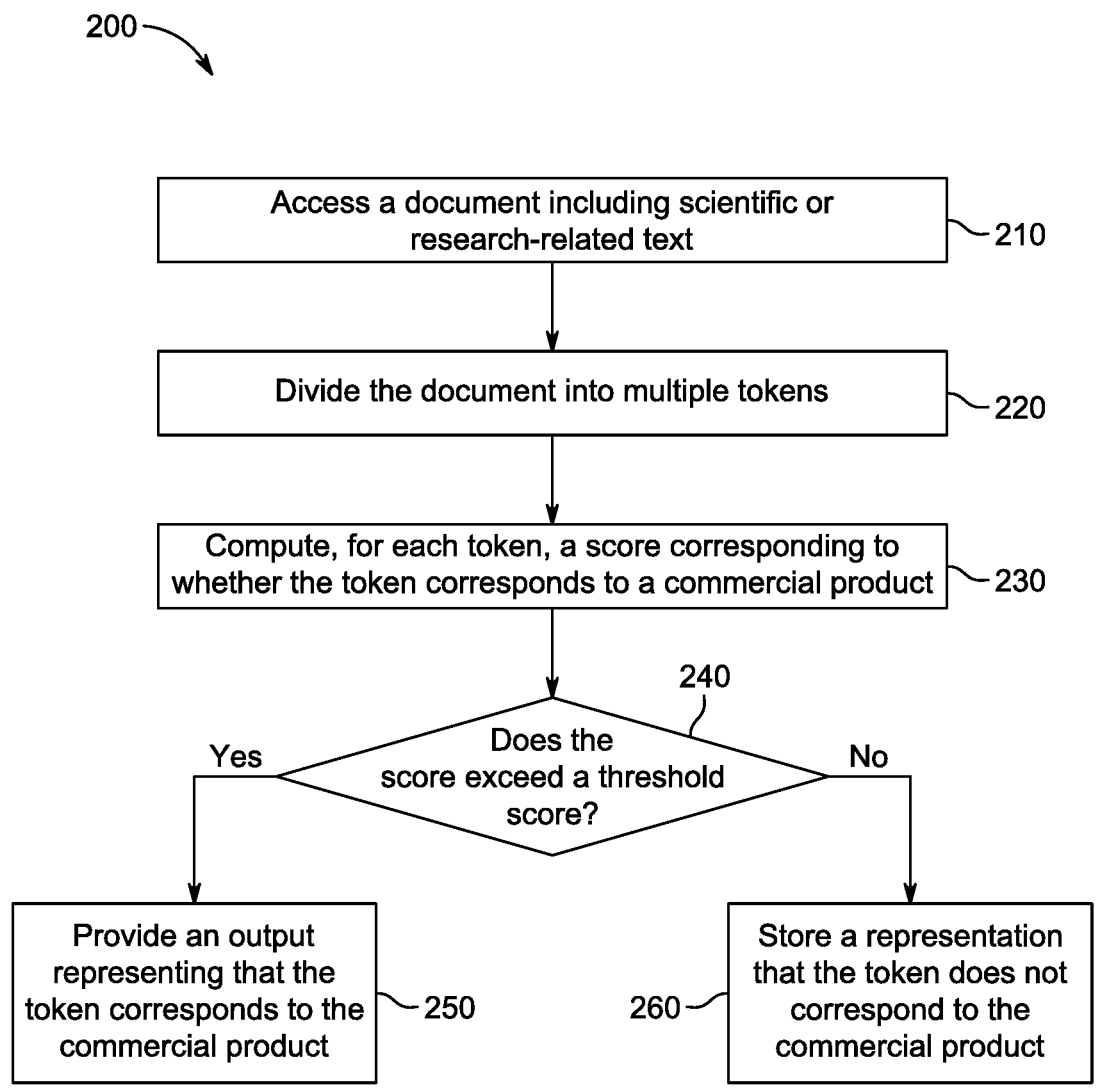
FIG. 2 is a flow chart of an example method for identifying a product in a document, according to some embodiments.

FIG. 2 is a flow chart of an example method 200 for identifying a product in a document. As described below, the method 200 is implemented at the server 120 within the system 100. However, the method 200 may be implemented by other machine(s) or in other environment(s).

Prior to implementing the method 200, the server 120 may be trained. In one example, the server 120 receives an input including multiple documents with identified commercial products within the documents. The commercial products may be identified using human readers of the documents. Each of the commercial products is identified by one or more of a product name, a catalog identification number, a manufacturer, and a location of the manufacturer. For example, the product name is "Microscope ABC," the catalog identification number is "X246," the manufacturer is "XYZ Inc." and the location of the manufacturer is "Boston, Mass." The server 120 is trained, using the multiple documents in the input, to compute the score/probability that each token in the document corresponds to a commercial product. As described in greater detail below, a token includes a part of the text that logically comprises a unit of information. For example, a comma and a dot are included in tokens, but "U.S.A." is just one token. The training of the server 120 may include any type of machine learning, for example, random forest, decision trees, and the like.

The method 200 begins at operation 210, where the server 120 accesses, from the database 130, a document including scientific or research-related text. The server 120 may access the document, for example, in response to a request to display the document at the client device 110 (e.g., via a browser application or via a special purpose application for accessing documents from the data repository 110).

At operation 220, the server 120 divides the document into multiple tokens. Each token includes a part of the text that logically comprises a unit of information. For example, in the text "We used Antibody A, Catalog number 123, manufactured by ABC Corporation of Dallas, Tex.," the tokens are set forth in Table 2.

TABLE 2

Tokens

We
Used
Antibody A,
Catalog number 123,
Manufactured
By
ABC Corporation
Of
Dallas, Texas The tokens, such as those listed in Table 2, are identified using machine learning. For example, text may be broken up into individual words based on the spaces between the words, and feature-based rules may then be applied to combine the words into tokens, with each token including one or more words. The rules may be identified using machine learning (e.g., providing the server 120 with a training set with human-identified tokens and training the machine to automatically identify the tokens itself by letting the machine discover features and rules whose application results in the automatic identification of tokens consistent with the human identification) or directly programmed into the server 120. Examples of rules used in generating the tokens of Table 2 include: "if the word 'Antibody' is capitalized in the middle of a sentence, the word 'Antibody' and the next word are a single token corresponding to the name of the antibody," "if the phrase 'Catalog number' is followed by a number or other alphanumeric identifier, the phrase 'Catalog number' and the next word are a single token corresponding to the catalog number," "if the word 'Corporation' is capitalized in the middle of a sentence, the word 'Corporation' and the previous word are a single token corresponding to a name of a business," and "a name of a city followed by a comma and a name of a state are a single token which corresponds to a geographic location." It should be noted that the machine may learn the rules using supervised machine learning, unsupervised machine learning, or a hybrid of supervised and unsupervised machine learning. Furthermore, the machine may discover the rules by itself, using a machine learning algorithm, rather than by having the rules set by a human operator of the machine.

At operation 230, the server 120 computes, for each token in the multiple tokens, a score corresponding to whether the token corresponds to a commercial product. The score may be a probability. The score is computed based on a list of features of commercial products and weights assigned to the features on the list. For example, a token that includes the word "Antibody" likely corresponds to an antibody. A token that includes a city or a state likely corresponds to a geographic location, and that geographic location may be associated with a product if it is proximate to other indicia of the product (e.g., as shown in Table 2). A token that includes the phrase "catalog number" followed by an alphanumeric code likely includes a catalog number of a product. The data used to tokenize the document and corresponding weights may be determined by machine learning. In one example, the score corresponding to whether an identified token corresponds to the commercial product is calculated based on a sum of the weights assigned to the token. In one example, weights assigned to neighboring tokens are also taken into account (e.g., if multiple commercial products are mentioned proximately to one another in a document).

The computation of the score/probability representing whether a token corresponds to the commercial products takes into account the identification of one or more of: a name of the commercial product, a catalog identification number, a manufacturer, and a location of the manufacturer. In some cases, the list of features includes textual features, syntactical features, and layout features. Textual features include the characters in the text. Syntactical features include features related to the arrangement of words to form sentences and phrases. For example, different syntax is used in a citation and in a paragraph of text of the body of the document. Layout features include size, font, bold/italic/underlined status of characters, as well as where on the page a character appears (e.g., on the top or on the bottom of the page, on the first line, on the first N lines, etc.). In some examples, the list of features includes one or more of: positions of capital letters within the token and whether the token includes capital letters, positions of punctuation marks within the token and whether the token includes punctuation marks, positions of digits within the token and whether the token includes digits, a length of the token, a word shape of the token, whether a string in the token belongs to a predetermined list of strings, and positions of italicized characters within the token. The predetermined list of strings may include a list of product names or a list of location names.

The list of features may be weighted, with some features being weighted more heavily than others. The weights may be determined by a conditional random field (CRF) machine learning algorithm.

In some cases, the server 120 computes the score/probability that the token corresponds to the commercial product by computing a score/probability that the token corresponds to a name, a catalog identification number, a manufacturer, and a location of the manufacturer corresponding to the commercial product. For example, the score/probability that a token correspond to the location of the manufacturer may be determined by comparing the token to a list of location names. The score/probability that the token corresponds to a product name may be determined by comparing the token to a list of product names.

At operation 240, the server 120 determines whether the score/probability that the token corresponds to the commercial product exceeds a threshold score/probability (e.g., 90%, 95% or 97%). If so, the method 200 continues to operation 250. If not, the method 200 continues to operation 260.

Figure 3:
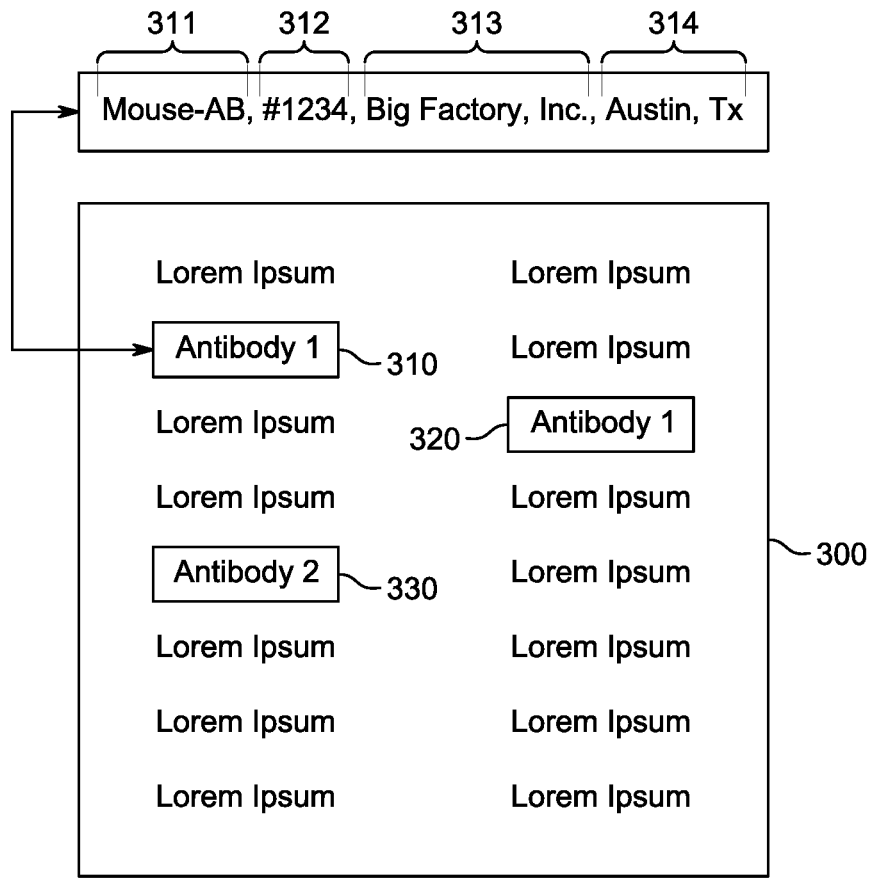
FIG. 3 illustrates an example document with identified products, according to some embodiments.

At operation 250, in response to determining that the score/probability exceeds the threshold score/probability, the server 120 provides an output representing that the token corresponds to the commercial product. For example, the output may be displayed at the client device 110 and may include highlighting or otherwise marking identified commercial product(s) in a document that includes scientific or research-related text. The token(s) representing the commercial product(s) may be converted into selectable links for displaying more information about the commercial product(s). One example of the output is shown in FIG. 3.

In some implementations, providing the output representing that the token corresponds to the commercial product includes marking (e.g., highlighting or otherwise marking) the token within the document to indicate that the token represents the commercial product, and providing, in response to a selection of the marked token, a sidebar display. The sidebar display, for example, as shown in FIG. 3, includes information related to the commercial product and a link to a page associated with the commercial product. The page associated with the commercial product may identify multiple documents that mention the commercial products. The multiple documents may be sortable by date, field of study, geographic location associated with creation of the document, and the like. In some cases, a popularity of the commercial product is determined based on a number of documents that mention the product in the multiple documents, with more popular commercial products being associated with multiple documents. After operation 250, the method 200 ends.

At operation 260, in response to determining that the score/probability does not exceed the threshold score/probability, the server 120 stores a representation that the token does not correspond to the commercial product. The representation may be stored in the data repository 130. After operation 260, the method 200 ends.

The subject technology may be implemented with multiple machine learning models. A first machine learning model detects products, using various sub-models to look for distinct product types and for domain-specific features. A second machine learning model detects the product type. Once the product type is detected, more specific models are run.

Figure 4:
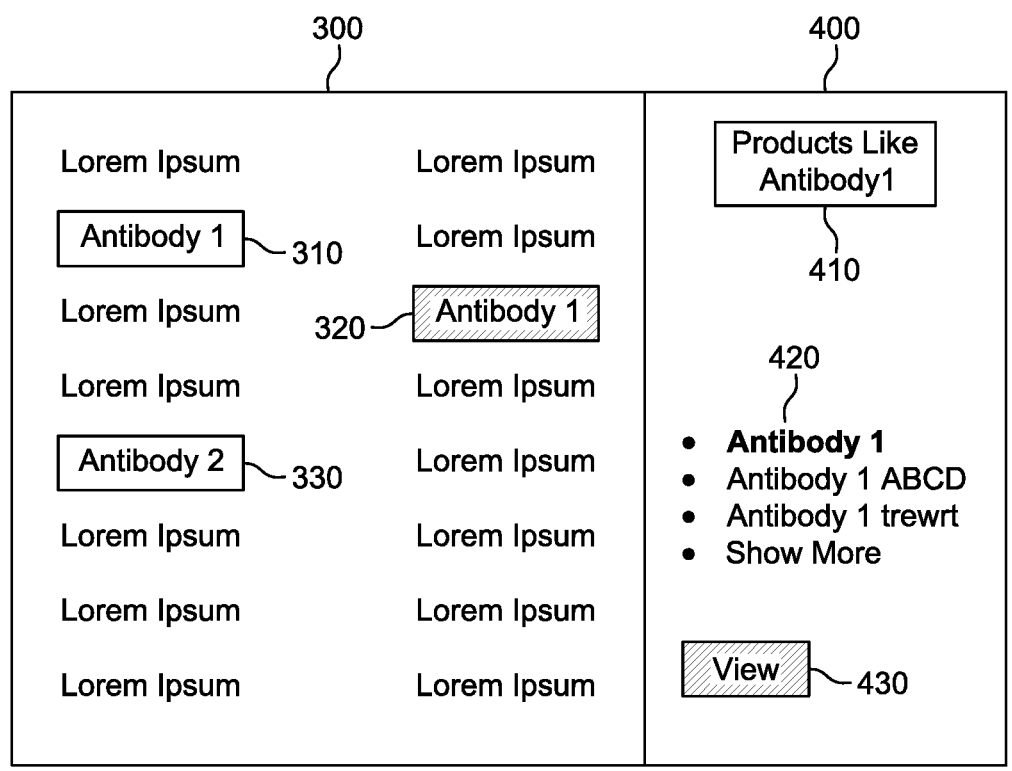
FIG. 4 illustrates an example document with a product sidebar for an identified product, according to some embodiments.

FIG. 3 illustrates an example document 300 with identified products. As shown, the document 300 includes text and identified commercial products 310, 320, and 330 at various points in the text. The commercial products 310 and 320 are "Antibody A," and the commercial product 300 is "Antibody B." The product identifications 310, 320, and 330 may be generated by the server 120, and the document 300 with the product identification 310, 320, and 330 may be provided for display at the client device 110, via operation of the server 120. In some cases, the user of the client device 110 displaying the document 300 may select one of the products 320. In response to the user's selection of the product 320, the interface of FIG. 4 is displayed. While the commercial products 310, 320, and 330 are identified, in FIG. 3, as "Antibody 1" or "Antibody 2," in some cases the commercial products may be identified using a more complex naming technique or citation that includes one or more of: a name, a catalog identification number, a manufacturer, or a location of the manufacturer. For instance, as shown, "Antibody 1" 310 corresponds to the name 311 ("Mouse-AB"), the catalog identification number 312 ("#1234"), the manufacturer 313 ("Big Factory, Inc."), and the location of the manufacturer 314 ("Austin, Tex.").

Each product 310, 320, and 330 may be identified by a product citations data model, as shown, for example, in Table 3.

TABLE 3

Product Citations Data Model

ObjectId id; // ID in mongo, not important users.
RgKey sourceId; // RgKey from document /q&a/... we found this in.
RgKey assetKey; // Which fulltext we took it from.
Long categoryId; // Denoting product type, e.g., antibodies, microscopes
String name;
String manufacturer;
String catalogNumber;
List features;
// e.g., antibodies: {host => "mouse", target_species => "human", target_antigen =>
String context;
// e.g., sentence(s)/ text snippets we extracted the product from
ProductMentionPaths contextPaths; // position of mention in sentence(s)
ProductMentionPaths assetPaths; // position of mention in PDF/ full text
Long productId; // if matchced, it will contain productId
Date creationDate;
Date lastModifiedDate;

To be able to reference documents and portions of documents, a document may be uniquely identified by a document key (e.g., RgKey in Table 3) and a portion of a document may be uniquely identified by a document path (e.g., RgPath). Various embodiments employ a combination of a document key uniquely identifying the publication and relevant version thereof, a document path specifying a certain portion or range of elements within the document and/or a grid of anchors distributed across the document that is robust to changes in the document and may facilitate referencing at an even finer level than the document elements afford.

The document key is generally canonical, i.e., stands in a bijective relationship to the document (or version of a document) it is referencing (e.g., such that each document or document version has only one key and each key identifies only one document or version). (In various embodiments, the document key is but one example of a more general "object key" used to identify any type of social object within the system, whether it be a user, item of content (e.g., publication, comment, etc.), or relation, for example) In some embodiments, the document key is composed of strong and weak entities. A strong entity stands on its own and maps to a particular publication (as identified, e.g., by its associated metadata) or other self-contained document, whereas a weak entity only exists (and may be unique only) in relation to a strong entity and references a version of the publication, a particular file or other separately stored item of content contained in the publication (herein "asset"), or an annotation, comment, or other item of content related to and associated with the publication. Various embodiments utilize string-based keys that are readable by both humans and machines. For example, the strong entity may be structured as a domain-identifying pre-fix, such as "PB," followed by a domain-internal unique identifier, such as "1001," such that publication 1001 is identified by key "PB:1001." The second asset within publication 1001 (which may be, e.g., a figure) may be referenced as "PA:2" following the strong entity portion, i.e., as "PB:1001:PA:2." Similarly, the third comment on the publication may be referenced, for instance, as "C:3" following the strong entity portion, i.e., as "PB:1001:C:3." The document keys may be language-independent, allowing a key, for example, to be generated in Java code and resolved in PHP. The document key, which is generally used internally to the system 100, may map onto a unique uniform resource identifier (URI) or digital object identifier (DOI) that facilitates referencing the document, in the correct version, outside the system 100. When a document originally published externally and already having an associated URI or DOI is uploaded to the system 100, the URI or DOI may be extracted and stored, e.g., as part of the publication metadata or in a separate bi-directional index of document keys and URI/DOIs. When a document is originally published in the data repository 130, the server 120 may generate and assign a URI or DOI to be stored in the metadata, an index, or otherwise in association with the document key. Either way, when a user accessing a particular version of a document in the system executes a user-interface element to cite the document, she may be automatically provided the associated URI or DOI.

While the document key can serve to reference a document (in a particular version) in its entirety, the document path facilitates pinpointing a piece of content within the document, such as, for instance, a particular paragraph or even an individual sentence or word therein. A document path is generally not canonical in that multiple different paths may lead to the same content within the document. (However, each path resolves, of course, to a unique portion of content.) For example, in some embodiments, documents are stored in the form of individual document elements, each identified by an associated document-element identifier, in conjunction with an ordered list of document elements representing the document in its entirety. In this case, the document path may specify a particular document element, or range of elements, in terms of the associated unique document-element identifiers. The same element or range of elements may be identified, alternatively, with reference to certain named portions of the document (e.g., the "materials and methods" section), in terms of page or paragraph numbers, and the like; this more human-readable referencing scheme, which is independent of the system-assigned element identifiers, is typically employed in external references to content maintained within the system, but may also be used internally.

In some embodiments, a referencing grid is generated for a document by creating a set of "anchors" dispersed throughout the document. Anchors are document elements without content that serve solely referencing purposes. Each anchor has its own unique document-element identifier and is stored in the document database just like any content-containing document element. Anchors may be placed between document elements as well as be nested within document elements. The latter may serve to localize references at a sub-element granularity. Assuming, for example, that each paragraph of text corresponds to a different document element, multiple anchors may be located within one document, e.g., at natural breakpoints of the paragraph, such as at the end of each sentence, or at punctuation marks or other markers associated with different parts of a sentence. Alternatively or additionally, anchors may be placed at regular intervals throughout the document (e.g., every five words). Using the grid of anchors, a portion of a document may be referenced in terms of these anchors, e.g., by specifying anchors associated with the starting and end points of the referenced portion.

In some cases, multiple products may be listed together, for example, in the same sentence (see, e.g., Table 4.1). For example, a scientific article may include a listing (e.g., in the same sentence) of multiple different antibodies (e.g., Antibody 1, Antibody 2, and Antibody 3 of Table 4.1) that were used in a research study. Each product may have a name (e.g., Antibody 1), a catalog identification number (e.g., 1234), a manufacturer (e.g., Big Factory, Inc.), and a location of the manufacturer (e.g., Austin, Tex.). Machine learning may be used to parse the list of multiple products into individual products. In some implementations, the listing of the products (e.g., antibodies) is divided into tokens. Each token is assigned, using a learning algorithm, a score/probability of being associated with a particular product named in the listing. The learning algorithm takes into account syntax, spacing, formatting, grammar, word shape, and any other token features (see, e.g., Table 5). In some cases, the pattern in which products are cited may be the same throughout a paper or a listing (e.g., name, followed by manufacturer, followed by catalog identification number). An example of the pattern in which products are cited being the same throughout the sentence is shown in the first row of Table 4.1. In other cases, the pattern may vary throughout the paper or throughout the listing, for example, as shown in the second and third rows of Table 4.1.

TABLE 4.1.

Example listings of products.

The following products were used: Antibody 1, #1234, Big Factory, Inc., Austin, TX; Antibody 2, #5678, Manufacturer, Co., Berlin, Germany; Antibody 3, #9012, Small Factory, Ltd., Boston, MA.
We used the products Antibody 1 (#1234, Big Factory, Inc.), Antibody 2 (Catalog No. 5678 of Manufacturer Co. in Berlin, Germany), and Antibody 3 (#9012 of Boston's Small Factory).
In addition to using Antibody 1 (#1234, Big Factory, Inc., Austin, TX), we also used Antibody 2 (#5678, Manufacturer Co.) and Antibody 3 (manufactured by Small Factory, Ltd., in Boston, MA).

Table 4.2 includes an example text to which learning algorithms may be applied. The text includes products, manufacturers, and locations. According to some aspects of the subject technology, there are two learning algorithms. A first learning algorithm breaks each sentence that mentions one or more products into sub-parts where for each part the following is true: the part contains at least one product and exactly one manufacturer. A second (machine) learning algorithm works on each subpart individually by: detecting a manufacturer, detecting one or more products, and associating those products to the detected manufacturer. In both cases the learning algorithm takes into account syntax, spacing, formatting, grammar, word shape, and any other token features.

TABLE 4.2

Example Text

"some text <product 1> some text <manufacturer 1> <location1> some text some text <product 1> <product 2> some text <manufacturer 1> <location 1> some text <product 1> <product 2> some text <manufacturer 1> <location 1> <manufacturer 2> <location 2>"

FIG. 4 illustrates the example document 300 of FIG. 3 with a product sidebar 400 for an identified product 320. As shown, the document 300 includes the products 310, 320, and 330, with the product 320 highlighted in response to the user's selection. Also, in response to the user's selection of the product 320, the sidebar 400 is displayed. The sidebar 400 includes information about the product 320, named "Antibody 1." The sidebar includes the identifier 410 reading, "Products like antibody 1," a list 420 of the products like antibody 1, and a view button 430, for viewing more information about antibody 1. In response to the selection of the view button 430, the interface of FIG. 5 is displayed.

Figure 5:
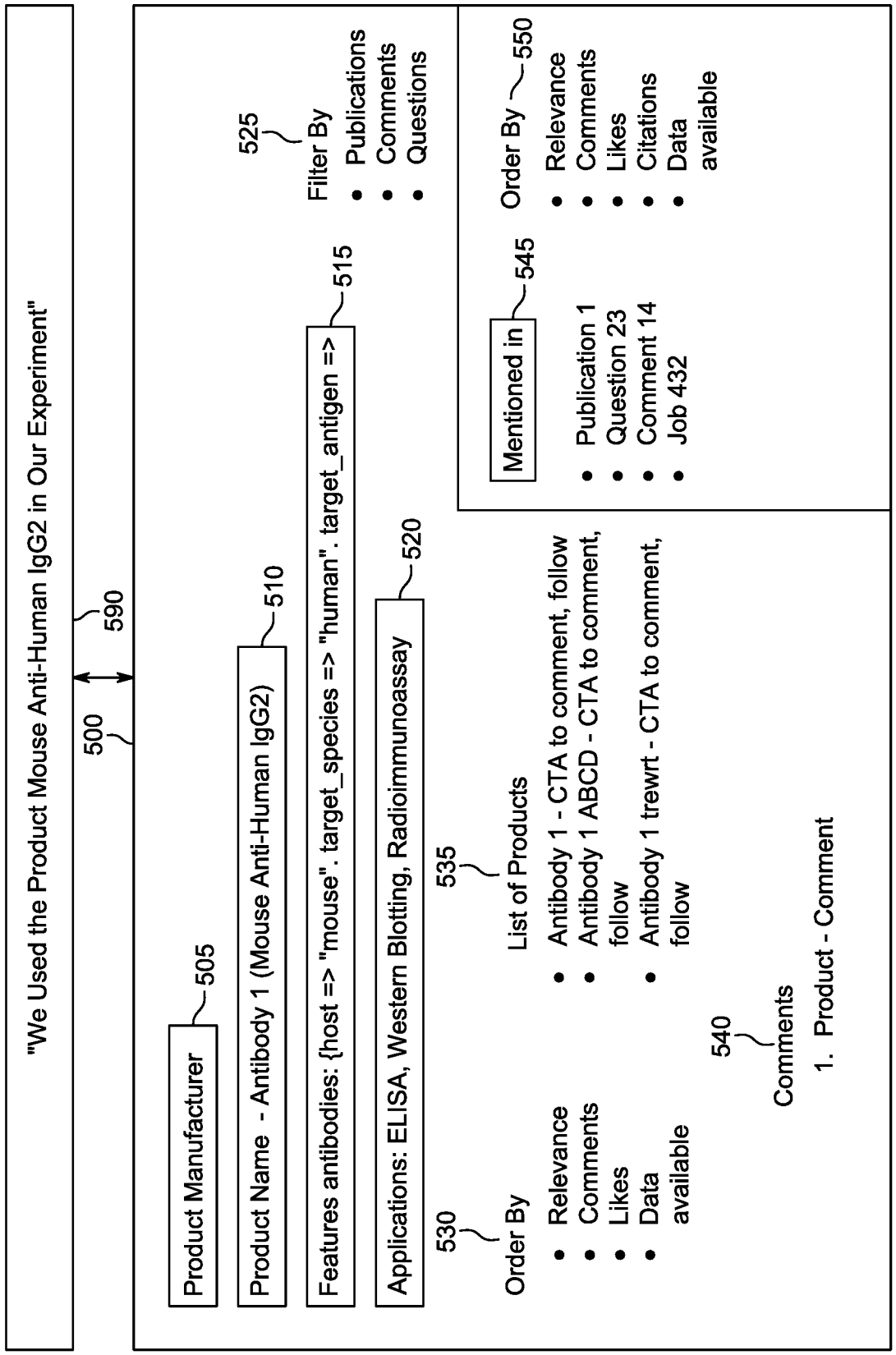
FIG. 5 illustrates an example dynamic product page, according to some embodiments.

FIG. 5 illustrates an example dynamic product page 500, which may be displayed in response to the selection of the view button 430. The dynamic product page 500 may be generated based on the sentence 590 in a document, such as a scientific research paper. As shown, the dynamic product page 500 includes an identification of the product manufacturer 505, an identification of the product name 510, key features 515 of the product, an identification of applications 520 of the product, a filtering interface 525 for a list of similar products, an ordering interface 530 for the list of similar products, the list of similar products 535, comments 540 about the product, a list of sources that mention the product 545, and an ordering interface 550 for the list of sources.

In accordance with some interfaces, commercial products stored in the data repository 130 may be searched based on a name string, a manufacturer string, a catalog number string, features, and whether the product is highlighted or in bold in a certain document. The results of the search may include links to dynamic product pages, such as the page 500.

The list of similar products 535 may include products similar to the product associated with the page 500. Products may be identified, for placement in the list 535, based on the features of the product associated with the page 500. For example, if the product is an antibody, the features may include a host body, a target species, and a targeted protein. Different features may be weighted differently based on a specification provided by a user (e.g., the user can indicate that he/she is interested in other antibodies with the same target species). In some cases, the products in the list 535 have at least N (where N is a positive integer) features in common with the product associated with the page 500. N may be greater than 1. Alternatively, N may be equal to 1. The specification may be provided via the ordering interface 530. Alternatively, as shown in FIG. 5, the ordering interface 530 may allow the user to order the list of products 535 by relevance, comments, likes, and data available. As used herein, the term "relevance" may include the number (N) of matching features. If all the features of a first product and a second product match, the first product may be an older/newer version of the second product, or the first product and the second product may be perfect substitute products from different manufacturers. The first product and the second product may correspond to a different version, packaging, or amount of the same thing.

The list of sources that mention the product 545 may include the source that provided the sentence 590. For example, the sentence 590 may be from "Publication 1" shown in the list of sources that mention the product 545. In some cases, the list of sources that mention the product 545 may show a quotation from the source (e.g., sentence 590) in addition to listing the titles. Alternatively, the quotation may be displayed in a hover card when the user hovers the mouse over each title. The hover card may include the sentence 590.

Figure 6:
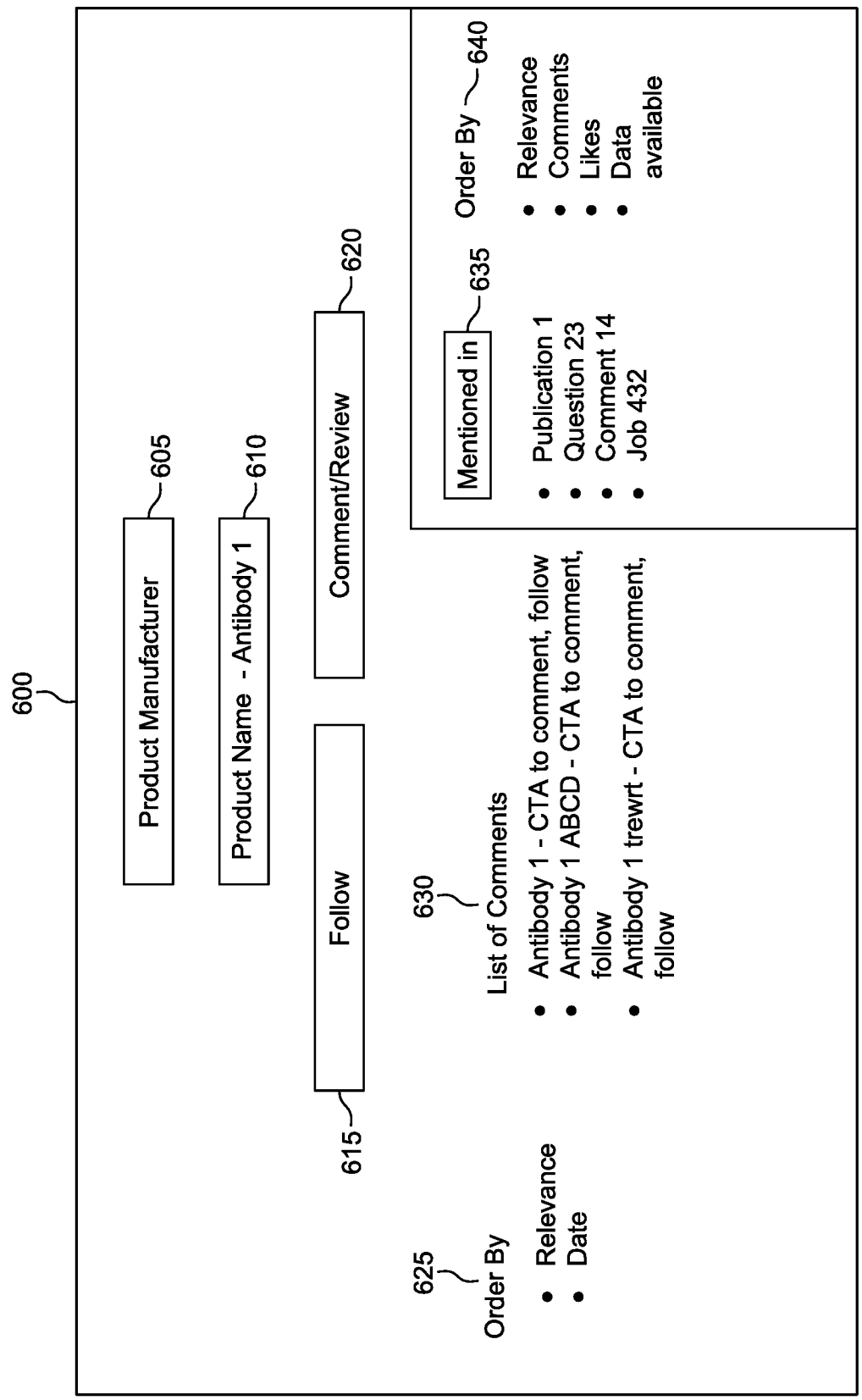
FIG. 6 illustrates an example product detail page, according to some embodiments.

FIG. 6 illustrates an example product detail page 600, according to some embodiments. The product detail page 600 may be presented at the client device 110 in response to the user's selection of the view button 430, in addition to or in place of the dynamic product page 500. As shown, the product detail page 600 identifies the product manufacturer 605 and the product name 610. The product detail page 600 includes links to follow 615 and to comment or review 620 the product. The product detail page 600 includes a list of comments 630 about the product and an ordering interface 625 for the list of comments. The product detail page 600 includes a list of mentions 635 of the product and an ordering interface 640 for the list of mentions.

Table 5 is a list of features of tokens, which may be used to identify a score/probability of whether a token corresponds to a product by using the presence and the weights of the features. Table 6 is a list of token types, which may be used in conjunction with the subject technology. The subject technology may have many use cases, for example, implementations may be used to count all products by a manufacturer, count all products by a type of manufacturer, or count all products by type. The subject technology may be used to identify where in text products are located, and to find products by features, application, or discussion in documents. The subject technology may make citation of commercial products in documents, such as research papers, more efficient. Table 5 is provided as an example only. Other features, in addition to those listed in Table 5, may also be used. Table 6 is provided as an example only. Other token types, in addition to those listed in Table 6, may also be used. The other types may be different from the <other> token listed in Table 6. The other types may be identified by machine learning and by identifying various product types.

TABLE 5

Token Feature List

Token itself
Lowercased token
Prefixes of length from 1 to 4
Suffixes of length from 1 to 4
Capitalization (Starts with capital letter, all caps, no caps)
Digit information: all digits, contains digits, no digits
Token is a single character: true, false
Punctuation type: no punctuation, bracket, dot, comma, hyphen, quote, other punctuation sign
Word shape
Token is in a list of known manufacturers, names of products or product categories
Token includes a notation associated with a product (e.g., antibody notation)
Domain knowledge-based features

TABLE 6

Token Types

<product> -- name of product
<manufacturer> -- name of manufacturer
<location> -- manufacturer's address
<id> -- catalog number
<other>

Figure 7:
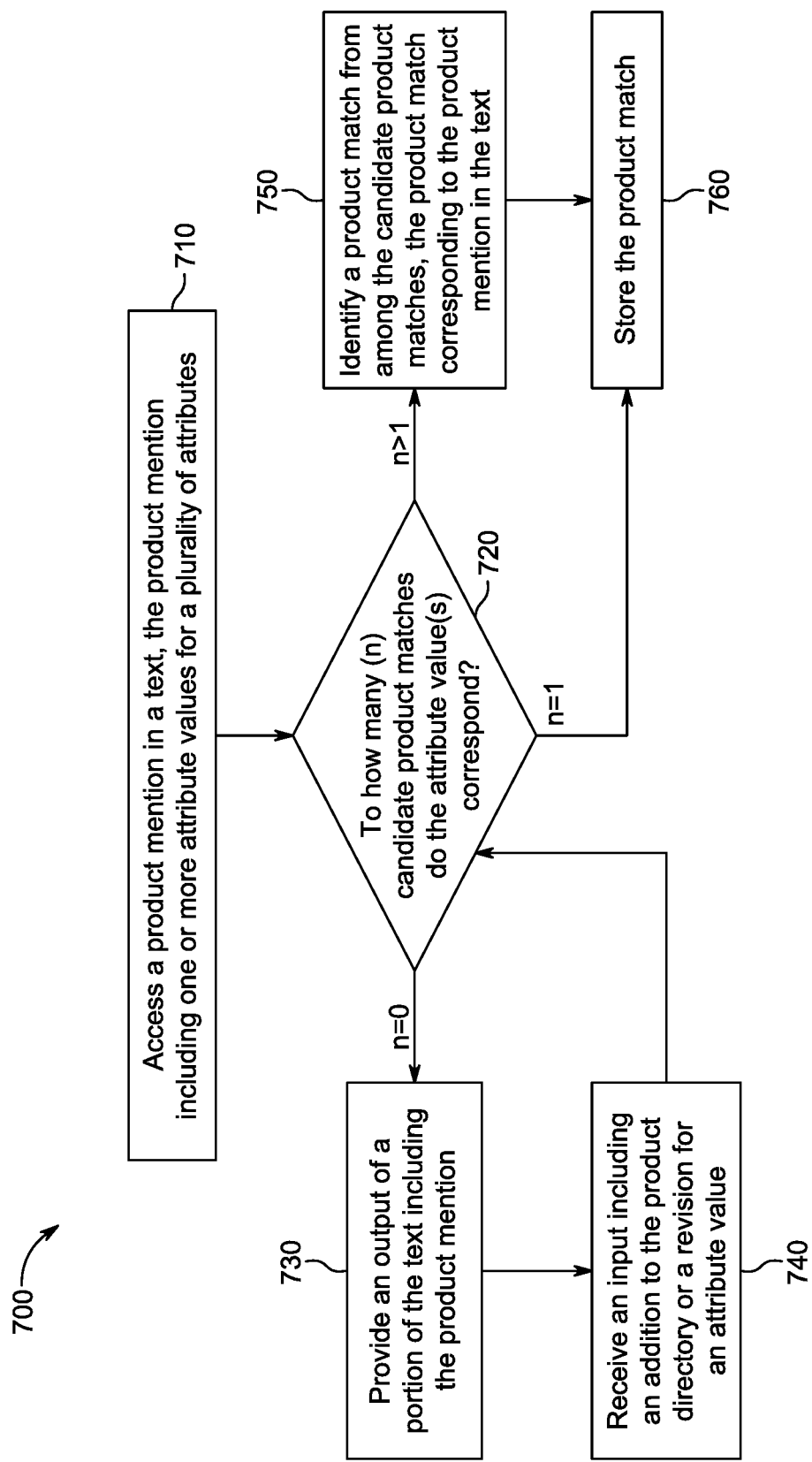
FIG. 7 is a flow chart of an example method for associating a product mention in a text with a product match in a product directory, according to some embodiments.

FIG. 7 is a flow chart of an example method 700 for associating a product mention in a text with a product match in a product directory, according to some embodiments. As described below, the method 700 is implemented at the server 120 within the system 100. However, the method 700 may be implemented by other machine(s) or in other environment(s).

At operation 710, the server 120 accesses a product mention in a scientific or research-related text (e.g., stored in the data repository 130). The product mention includes one or more attribute values for a plurality of attributes. Each attribute value is associated with either a single attribute value or no attribute value. The plurality of attributes may include one or more of a name, a catalog identification number, a manufacturer, and a location of the manufacturer. Examples of texts including product mentions are shown in Table 4.1. In one example from Table 4.1, in the text, "we also used Antibody 2 (#5678, Manufacturer Co.)," the attribute name is mapped to "Antibody 2," the attribute catalog identification number is mapped to "#5678," the attribute manufacturer is mapped to "Manufacturer Co.," and the attribute location of the manufacturer is not mapped to any value.

At operation 720, the server 120 determines to how many (n) candidate product matches the attribute value(s) of the product mention correspond. The candidate product matches are stored in a product directory. The product directory may be stored in the data repository 130. The product directory may include one or more product catalogs from one or more manufacturers. The product catalogs may list products that are available in different geographic regions, at the current time, and/or at various times in the past. If n=0, the method 700 continues to operation 730. If n=1, the method 700 continues to operation 760. If n>1, the method 700 continues to operation 750.

At operation 730, if n=0 (in other words, the server 120 has determined that there are no candidate product matches in the product directory that correspond to the attribute value(s)), the server 120 provides, via the network 140 (e.g., to the client device(s) 110), an output of a portion of the scientific or research-related text including the product mention.

At operation 740, the server 120 receives, via the network 140 and in response to the output of operation 730, an input including an addition to the product directory (e.g., a new catalog or entry for the product directory) or a revision of an attribute value of the product mention. The addition to the product directory may include fixing an omission in the product directory or correcting an entry in the product directory. After operation 740, the method 700 returns to operation 720, and the number (n) of candidate product matches to which the attribute value(s) of the product mention correspond is adjusted based on the input of operation 740.

At operation 750, if n>1 (in other words, the server 120 has determined that there is more than one candidate product match in the product directory that corresponds to the attribute value(s)), the server 120 identifies, based at least in part on stored data related to the scientific or research-related text, a product match from among the candidate product matches. The product match corresponds to the product mention in the scientific or research-related text.

In some cases, the server 120 identifies the product match from among the candidate product matches by: identifying one or more other scientific or research-related texts citing one or more of the candidate product matches and sharing one or more characteristics of the scientific or research-related text that includes the product mention, and identifying, from among the candidate product matches, a subset corresponding to the candidate product matches cited in the one or more other scientific or research-related texts. The product match is identified from the subset. The characteristics may include at least one of: one or more authors, an institutional affiliation of the one or more authors, a geographic region of the one or more authors, a time-frame of publication, and a topic of the scientific or research-related text.

In some cases, the server 120 identifies the product match from among the candidate product matches by: identifying, from among the candidate product matches and based on information stored in the product directory, a subset comprising candidate product matches sharing characteristics with the scientific or research-related text. The product match is identified from the subset. The characteristics may include at least one of: availability at a time before a publication date of the scientific or research-related text and availability in a geographic region associated with an author of the scientific or research-related text.

In some cases, the server 120 identifies the product match from among the candidate product matches by: providing, via the network 140 (e.g., to the client device(s) 110) an output of at least a subset of the candidate product matches. The server 120 receives, via the network 140 and in response to the output, an indication of the identified product match. In some examples, the server 120 computes, for each candidate product match, a score representing a likelihood (or a probability) that the candidate product match is the product match. The server 120 arranges the candidate product matches in an ordered list based on the score. The output described above includes the ordered list.

At operation 760, the server 120 provides an output (e.g., to the data repository 130 or via the network 140) of the product match for storage in conjunction with the product mention in the scientific or research-related text. The operation 760 may follow the operation 750 if n>1. Alternatively, if n=1, the operation 760 may be implemented as the next operation after the single candidate product match (which corresponds to the product match) is identified at operation 720. After operation 760, the method 700 ends.

Figure 8:
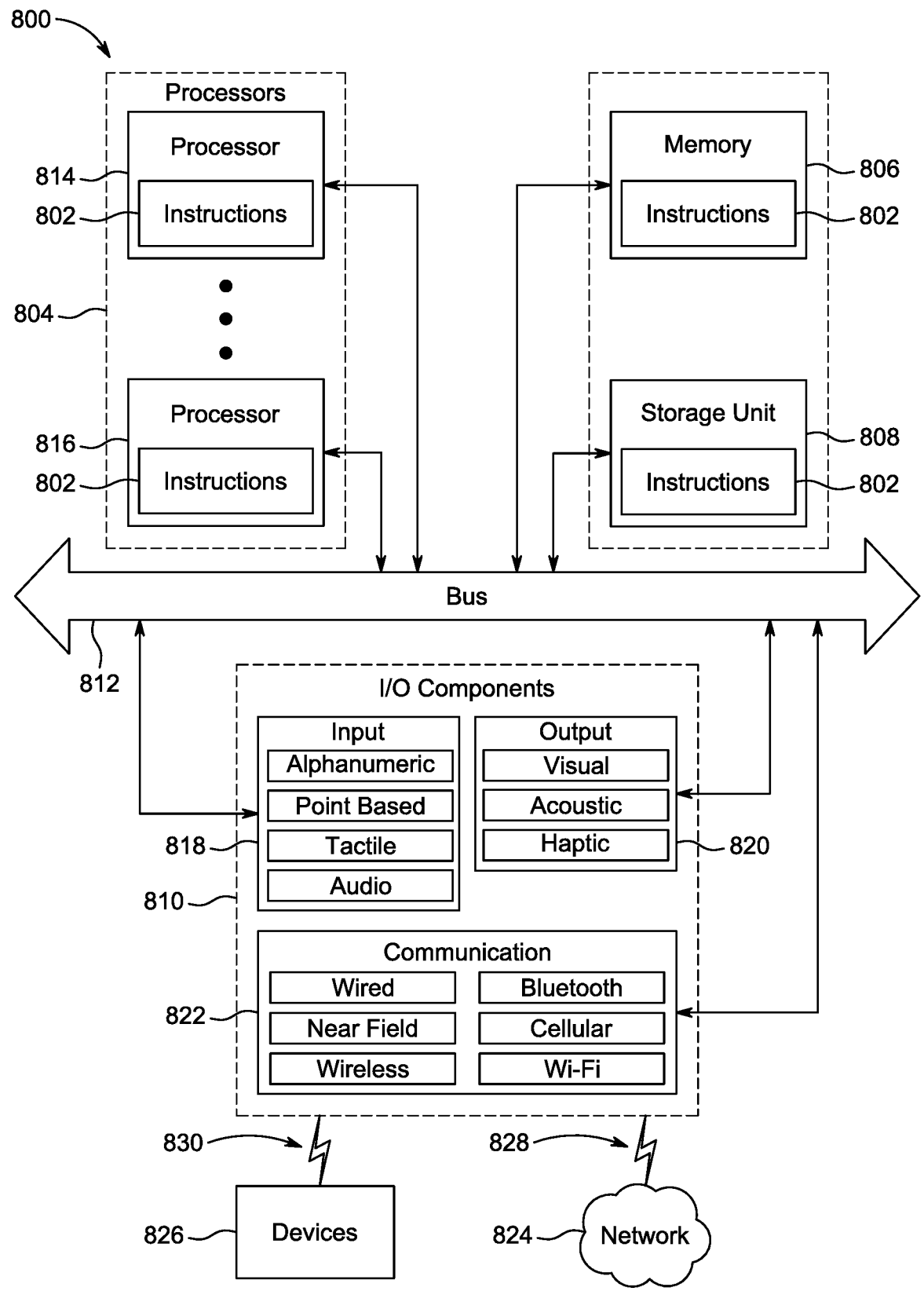
FIG. 8 is a block diagram illustrating components of an example machine able to read instructions from a machine-readable medium, according to some embodiments.

FIG. 8 is a block diagram illustrating components of a machine 800, according to some example embodiments, able to read instructions from a machine-readable medium (e.g., a machine-readable storage medium) and perform any one or more of the methodologies discussed herein. The machine 800 may correspond to one or more of the machines 110, 120, and 130 of FIG. 1. Specifically, FIG. 8 shows a diagrammatic representation of the machine 800 in the example form of a system within which instructions 802 (e.g., software, a program, an application, an applet, an app, a driver, or other executable code) for causing the machine 800 to perform any one or more of the methodologies discussed herein may be executed. For example, the instructions 802 include executable code that causes the machine 800 to execute the method 200 or the method 700. In this way, these instructions transform the general, non-programmed machine into a particular machine programmed to carry out the described and illustrated functions in the manner described herein. The machine 800 may operate as a standalone device or may be coupled (e.g., networked) to other machines.

By way of non-limiting example, the machine 800 may comprise or correspond to a television, a computer (e.g., a server computer, a client computer, a personal computer (PC), a tablet computer, a laptop computer, or a netbook), a set-top box (STB), a personal digital assistant (PDA), an entertainment media system (e.g., an audio/video receiver), a cellular telephone, a smart phone, a mobile device, a wearable device (e.g., a smart watch), a portable media player, or any machine capable of outputting audio signals and capable of executing the instructions 802, sequentially or otherwise, that specify actions to be taken by machine 800. Further, while only a single machine 800 is illustrated, the term "machine" shall also be taken to include a collection of machines 800 that individually or jointly execute the instructions 802 to perform any one or more of the methodologies discussed herein.

The machine 800 may include processors 804, memory 806, storage unit 808 and I/O components 810, which may be configured to communicate with each other such as via a bus 812. In an example embodiment, the processors 804 (e.g., a central processing unit (CPU), a reduced instruction set computing (RISC) processor, a complex instruction set computing (CISC) processor, a graphics processing unit (GPU), a digital signal processor (DSP), an application specific integrated circuit (ASIC), a radio-frequency integrated circuit (RFIC), another processor, or any suitable combination thereof) may include, for example, processor 814 and processor 816 that may execute instructions 802. The term "processor" is intended to include multi-core processors that may comprise two or more independent processors (sometimes referred to as "cores") that may execute instructions contemporaneously. Although FIG. 8 shows multiple processors, the machine 800 may include a single processor with a single core, a single processor with multiple cores (e.g., a multi-core process), multiple processors with a single core, multiple processors with multiples cores, or any combination thereof.

The memory 806 (e.g., a main memory or other memory storage) and the storage unit 808 are both accessible to the processors 804 such as via the bus 812. The memory 806 and the storage unit 808 store the instructions 802 embodying any one or more of the methodologies or functions described herein. In some embodiments, the database 86 resides on the storage unit 808. The instructions 802 may also reside, completely or partially, within the memory 806, within the storage unit 808, within at least one of the processors 804 (e.g., within the processor's cache memory), or any suitable combination thereof, during execution thereof by the machine 800. Accordingly, the memory 806, the storage unit 808, and the memory of processors 804 are examples of machine-readable media.

As used herein, "machine-readable medium" means a device able to store instructions and data temporarily or permanently and may include, but is not be limited to, random-access memory (RAM), read-only memory (ROM), buffer memory, flash memory, optical media, magnetic media, cache memory, other types of storage (e.g., erasable programmable read-only memory (EEPROM)), or any suitable combination thereof. The term "machine-readable medium" should be taken to include a single medium or multiple media (e.g., a centralized or distributed database, or associated caches and servers) able to store instructions 802. The term "machine-readable medium" shall also be taken to include any medium, or combination of multiple media, that is capable of storing instructions (e.g., instructions 802) for execution by a machine (e.g., machine 800), such that the instructions, when executed by one or more processors of the machine 800 (e.g., processors 804), cause the machine 800 to perform any one or more of the methodologies described herein (e.g., method 200 or method 700). Accordingly, a "machine-readable medium" refers to a single storage apparatus or device, as well as "cloud-based" storage systems or storage networks that include multiple storage apparatus or devices. The term "machine-readable medium" excludes signals per se.

Furthermore, the "machine-readable medium" is non-transitory in that it does not embody a propagating signal. However, labeling the tangible machine-readable medium as "non-transitory" should not be construed to mean that the medium is incapable of movement-the medium should be considered as being transportable from one real-world location to another. Additionally, since the machine-readable medium is tangible, the medium may be considered to be a machine-readable device.

The I/O components 810 may include a wide variety of components to receive input, provide output, produce output, transmit information, exchange information, capture measurements, and so on. The specific I/O components 810 that are included in a particular machine will depend on the type of machine. For example, portable machines such as mobile phones will likely include a touch input device or other such input mechanisms, while a headless server machine will likely not include such a touch input device. It will be appreciated that the I/O components 810 may include many other components that are not specifically shown in FIG. 8. The I/O components 810 are grouped according to functionality merely for simplifying the following discussion and the grouping is in no way limiting. In various example embodiments, the I/O components 810 may include input components 818 and output components 820. The input components 818 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components, and the like. The output components 820 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth.

Communication may be implemented using a wide variety of technologies. The I/O components 810 may include communication components 822 operable to couple the machine 800 to a network 824 or devices 826 via coupling 828 and coupling 830, respectively. For example, the communication components 822 may include a network interface component or other suitable device to interface with the network 824. In further examples, communication components 822 may include wired communication components, wireless communication components, cellular communication components, near field communication (NFC) components, Bluetooth® components (e.g., Bluetooth® Low Energy), WiFi® components, and other communication components to provide communication via other modalities. The devices 826 may be another machine or any of a wide variety of peripheral devices (e.g., a peripheral device coupled via a Universal Serial Bus (USB)).

The subject technology is described below in various clauses. The clauses are provided as examples only and do not limit the subject technology.

Clause 1 is a method comprising: accessing, at a computing machine, a document including scientific or research-related text; dividing the document into a plurality of tokens, each token comprising a part of the text that logically comprises a unit of information; computing, for each token in the plurality of tokens, a score corresponding to whether the token corresponds to a commercial product, the score being computed based on a list of features of commercial products and weights assigned to features in the list; determining that the score exceeds a threshold score; and providing, in response to determining that the score exceeds the threshold score, an output representing that the token corresponds to the commercial product.

Clause 2 is the method of clause 1, wherein the score corresponding to whether the token corresponds to the commercial product comprises a probability that the token corresponds to the commercial product.

Clause 3 is the method of clause 1, further comprising: receiving, at the computing machine, an input comprising plural documents with identified commercial products within the documents; and training the computing machine to compute the score corresponding to whether the token corresponds to the commercial product using the input.

Clause 4 is the method of clause 3, wherein the identified commercial products are identified by one or more of: a name, a catalog identification number, a manufacturer, and a location of the manufacturer.

Clause 5 is the method of clause 1, wherein the list of features comprises textual features, syntactical features, and layout features.

Clause 6 is the method of clause 1, wherein the list of features comprises: positions of capital letters within the token and whether the token includes capital letters, positions of punctuation marks within the token and whether the token includes punctuation marks, positions of digits within the token and whether the token includes digits, a length of the token, a word shape of the token, whether a string in the token belongs to a predetermined list of strings, and positions of italicized characters within the token.

Clause 7 is the method of clause 6, wherein the predetermined list of strings comprises a list of product names or a list of location names.

Clause 8 is the method of clause 1, wherein computing the score corresponding to whether the token corresponds to the commercial product comprises: computing a score corresponding to whether the token corresponds to a name of a product, a catalog identification number of a product, a manufacturer of a product, or a location of the manufacturer.

Clause 9 is the method of clause 1, wherein providing the output representing that the token corresponds to the commercial product comprises: marking the token within the document to indicate that the token represents the commercial product; and providing, in response to a selection of the marked token, a sidebar display, wherein the sidebar display comprises information related to the commercial product and a link to a page associated with the commercial product.

Clause 10 is the method of clause 9, wherein the page associated with the commercial product identifies a plurality of documents that mention the commercial product, the plurality of documents being sortable by date, field of study, and geographic location.

Clause 11 is the method of clause 10, further comprising: determining a popularity of the commercial product based on a number of documents that mention the product in the plurality of documents.

Clause 12 is a non-transitory machine-readable medium comprising instructions which, when executed by a computing machine, cause the computing machine to implement operations comprising: accessing, at the computing machine, a document including scientific or research-related text; dividing the document into a plurality of tokens, each token comprising a part of the text that logically comprises a unit of information; computing, for each token in the plurality of tokens, a score corresponding to whether the token corresponds to a commercial product, the score being computed based on a list of features of commercial products and weights assigned to features in the list; determining that the score exceeds a threshold score; and providing, in response to determining that the score exceeds the threshold score, an output representing that the token corresponds to the commercial product.

Clause 13 is the machine-readable medium of clause 12, the operations further comprising: receiving, at to the computing machine, an input comprising plural documents with identified commercial products within the documents; and training the computing machine to compute the score corresponding to whether the token corresponds to the commercial product using the input.

Clause 14 is the machine-readable medium of clause 13, wherein the identified commercial products are identified by one or more of: a name, a catalog identification number, a manufacturer, and a location of the manufacturer.

Clause 15 is the machine-readable medium of clause 12, wherein the list of features comprises textual features, syntactical features, and layout features.

Clause 16 is the machine-readable medium of clause 12, wherein the list of features comprises: positions of capital letters within the token and whether the token includes capital letters, positions of punctuation marks within the token and whether the token includes punctuation marks, positions of digits within the token and whether the token includes digits, a length of the token, a word shape of the token, whether a string in the token belongs to a predetermined list of strings, and positions of italicized characters within the token.

Clause 17 is the machine-readable medium of clause 12, wherein computing the score corresponding to whether the token corresponds to the commercial product comprises: computing a score corresponding to whether the token corresponds to a name of a product, a catalog identification number of a product, a manufacturer of a product, or a location of the manufacturer.

Clause 18 is a system comprising: one or more processors of a computing machine; and a memory comprising instructions which, when executed by the one or more processors, cause the computing machine to implement operations comprising: accessing, at the computing machine, a document including scientific or research-related text; dividing the document into a plurality of tokens, each token comprising a part of the text that logically comprises a unit of information; computing, for each token in the plurality of tokens, a score corresponding to whether the token corresponds to a commercial product, the score being computed based on a list of features of commercial products and weights assigned to features in the list; determining that the score exceeds a threshold score; and providing, in response to determining that the score exceeds the threshold score, an output representing that the token corresponds to the commercial product.

Clause 19 is the system of clause 18, the operations further comprising: receiving, at the computing machine, an input comprising plural documents with identified commercial products within the documents; and training the computing machine to compute the score that the token corresponds to the commercial product using the input.

Clause 20 is the system of clause 19, wherein the identified commercial products are identified by one or more of: a name, a catalog identification number, a manufacturer, and a location of the manufacturer.

Clause 21 is a method comprising: accessing, at a computing machine, a product mention in a scientific or research-related text, the product mention including one or more attribute values for a plurality of attributes, each attribute being associated with either a single attribute value or no attribute value; determining that the attribute values of the product mention correspond to two or more candidate product matches in a product directory; identifying, at the computing machine and based at least in part on stored data related to the scientific or research-related text, a product match from among the candidate product matches, the product match corresponding to the product mention in the scientific or research-related text; and providing an output of the product match for storage in conjunction with the product mention in the scientific or research-related text.

Clause 22 is the method of clause 21, wherein identifying the product match from among the candidate product matches comprises: identifying one or more other scientific or research-related texts citing one or more of the candidate product matches and sharing one or more characteristics of the scientific or research-related text that includes the product mention; identifying, from among the candidate product matches, a subset corresponding to the candidate product matches cited in the one or more other scientific or research-related texts; and identifying the product match from the subset.

Clause 23 is the method of clause 22, the characteristics comprising at least one of: one or more authors, an institutional affiliation of the one or more authors, a geographic region of the one or more authors, a time-frame of publication, and a topic of the scientific or research-related text.

Clause 24 is the method of clause 21, wherein identifying the product match from among the candidate product matches comprises: identifying, from among the candidate product matches and based on information stored in the product directory, a subset comprising candidate product matches sharing characteristics with the scientific or research-related text; and identifying the product match from the subset.

Clause 25 is the method of clause 24, the characteristics comprising at least one of: availability at a time before a publication date of the scientific or research-related text and availability in a geographic region associated with an author of the scientific or research-related text.

Clause 26 is the method of clause 21, wherein identifying the product match from among the candidate product matches comprises: providing, via a network, an output of at least a subset of the candidate product matches; and receiving, via the network and in response to the output, an indication of the identified product match.

Clause 27 is the method of clause 26, further comprising: computing, for each candidate product match, a score representing a likelihood that the candidate product match is the product match; and arranging the two or more candidate product matches in an ordered list based on the score, wherein the output includes the ordered list.

Clause 28 is the method of clause 27, wherein the score represents a probability that the candidate product match is the product match.

Clause 29 is the method of clause 21, further comprising: determining that the attribute values of the product mention do not correspond to any candidate product matches in a product directory; providing, via a network, an output of a portion of the scientific or research-related text including the product mention; and receiving, via the network and in response to the output, an input comprising an addition to the product directory or a revision for an attribute value of the product mention, wherein determining that the attribute values of the product mention correspond to the two or more candidate product matches in the product directory is in response to the input.

Clause 30 is the method of clause 21, wherein the plurality of attributes include: a name, a catalog identification number, a manufacturer, and a location of the manufacturer.

Clause 31 is the method of clause 21, wherein the product directory comprises one or more product catalogs from one or more manufacturers.

Clause 32 is a system comprising: one or more processors of a computing machine; and a memory comprising instructions which, when executed by the one or more processors, cause the computing machine to implement operations comprising: accessing, at the computing machine, a product mention in a scientific or research-related text, the product mention including one or more attribute values for a plurality of attributes, each attribute being associated with either a single attribute value or no attribute value; determining that the attribute values of the product mention correspond to two or more candidate product matches in a product directory; identifying, at the computing machine and based at least in part on stored data related to the scientific or research-related text, a product match from among the candidate product matches, the product match corresponding to the product mention in the scientific or research-related text; and providing an output of the product match for storage in conjunction with the product mention in the scientific or research-related text.

Clause 33 is a non-transitory machine-readable medium comprising instructions which, when executed by a computing machine, cause the computing machine to implement operations comprising: accessing, at the computing machine, a product mention in a scientific or research-related text, the product mention including one or more attribute values for a plurality of attributes, each attribute being associated with either a single attribute value or no attribute value; determining that the attribute values of the product mention correspond to two or more candidate product matches in a product directory; identifying, at the computing machine and based at least in part on stored data related to the scientific or research-related text, a product match from among the candidate product matches, the product match corresponding to the product mention in the scientific or research-related text; and providing an output of the product match for storage in conjunction with the product mention in the scientific or research-related text.

Clause 34 is the machine-readable medium of clause 33, wherein identifying the product match from among the candidate product matches comprises: identifying one or more other scientific or research-related texts citing one or more of the candidate product matches and sharing one or more characteristics of the scientific or research-related text that includes the product mention; identifying, from among the candidate product matches, a subset corresponding to the candidate product matches cited in the one or more other scientific or research-related texts; and identifying the product match from the subset.

Clause 35 is the machine-readable medium of clause 34, the characteristics comprising at least one of: one or more authors, an institutional affiliation of the one or more authors, a geographic region of the one or more authors, a time-frame of publication, and a topic of the scientific or research-related text.

Clause 36 is the machine-readable medium of clause 33, wherein identifying the product match from among the candidate product matches comprises: identifying, from among the candidate product matches and based on information stored in the product directory, a subset comprising candidate product matches sharing characteristics with the scientific or research-related text; and identifying the product match from the subset.

Clause 37 is the machine-readable medium of clause 36, the characteristics comprising at least one of: availability at a time before a publication date of the scientific or research-related text and availability in a geographic region associated with an author of the scientific or research-related text.

Clause 38 is the machine-readable medium of clause 33, wherein identifying the product match from among the candidate product matches comprises: providing, via a network, an output of at least a subset of the candidate product matches; and receiving, via the network and in response to the output, an indication of the identified product match.

Clause 39 is the machine-readable medium of clause 38, further comprising: computing, for each candidate product match, a score representing a likelihood that the candidate product match is the product match; arranging the two or more candidate product matches in an ordered list based on the score, wherein the output includes the ordered list.

Clause 40 is the machine-readable medium of clause 33, further comprising: determining that the attribute values of the product mention do not correspond to any candidate product matches in a product directory; providing, via a network, an output of a portion of the scientific or research-related text including the product mention; and receiving, via the network and in response to the output, an input comprising an addition to the product directory or a revision for an attribute value of the product mention, wherein determining that the attribute values of the product mention correspond to the two or more candidate product matches in the product directory is in response to the input.

Clause 41 is a method comprising: accessing, at a computing machine, a product mention in a scientific or research-related text, the product mention including one or more attribute values for a plurality of attributes, each attribute being associated with either a single attribute value or no attribute value; determining that the attribute values of the product mention do not correspond to any candidate product matches in a product directory; providing, via a network, an output of a portion of the scientific or research-related text including the product mention; receiving, via the network and in response to the output, an input comprising an addition to the product directory or a revision for an attribute value of the product mention; determining that the attribute values of the product mention correspond to one product match in the product directory in response to the input; and providing an output of the product match for storage in conjunction with the product mention in the scientific or research-related text.

Clause 42 is the method of claim 41, wherein the addition to the product directory comprises fixing an omission in the product directory.

Clause 43 is the method of claim 41, wherein the addition to the product directory comprises correcting an entry in the product directory.

Clause 44 is a system comprising: one or more processors of a computing machine; and a memory comprising instructions which, when executed by the one or more processors, cause the computing machine to implement operations comprising: accessing, at the computing machine, a product mention in a scientific or research-related text, the product mention including one or more attribute values for a plurality of attributes, each attribute being associated with either a single attribute value or no attribute value; determining that the attribute values of the product mention do not correspond to any candidate product matches in a product directory; providing, via a network, an output of a portion of the scientific or research-related text including the product mention; receiving, via the network and in response to the output, an input comprising an addition to the product directory or a revision for an attribute value of the product mention; determining that the attribute values of the product mention correspond to one product match in the product directory in response to the input; and providing an output of the product match for storage in conjunction with the product mention in the scientific or research-related text.

Clause 45 is a non-transitory machine-readable medium comprising instructions which, when executed by a computing machine, cause the computing machine to implement operations comprising: accessing, at the computing machine, a product mention in a scientific or research-related text, the product mention including one or more attribute values for a plurality of attributes, each attribute being associated with either a single attribute value or no attribute value; determining that the attribute values of the product mention do not correspond to any candidate product matches in a product directory; providing, via a network, an output of a portion of the scientific or research-related text including the product mention; receiving, via the network and in response to the output, an input comprising an addition to the product directory or a revision for an attribute value of the product mention; determining that the attribute values of the product mention correspond to one product match in the product directory in response to the input; and providing an output of the product match for storage in conjunction with the product mention in the scientific or research-related text.

The above-described features and applications can be implemented as software processes that are specified as a set of instructions recorded on a computer-readable storage medium (also referred to as computer-readable medium). When these instructions are executed by one or more processor(s) (which may include, for example, one or more processors, cores of processors, or other processing units), they cause the processor(s) to perform the actions indicated in the instructions. Examples of computer-readable media include, but are not limited to, CD-ROMs, flash drives, RAM chips, hard drives, erasable programmable read-only memory (EPROM), etc. In some cases, the computer-readable media does not include carrier waves and electronic signals passing wirelessly or over wired connections. Alternatively, the computer-readable media includes carrier waves or electronic signals passing wirelessly or over wired connections.

In this specification, the term "software" is meant to include firmware residing in read-only memory or applications stored in magnetic storage or flash storage, for example, a solid-state drive, which can be read into memory for processing by a processor. Also, in some implementations, multiple software technologies can be implemented as sub-parts of a larger program while remaining distinct software technologies. In some implementations, multiple software technologies can also be implemented as separate programs. Finally, any combination of separate programs that together implement a software technology described here is within the scope of the subject technology. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, for example microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic or solid state hard drives, read-only and recordable Blu-Ray® discs, ultra-density optical discs, any other optical or magnetic media, and floppy disks. The computer-readable media can store a computer program that is executable by at least one processor and includes sets of instructions for performing various operations. Examples of computer programs or computer code include machine code, for example is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, for example application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms "display" or "displaying" mean displaying on an electronic device. As used in this specification and any claims of this application, the terms "computer-readable medium" and "computer-readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a cathode ray tube (CRT) or liquid crystal display (LCD) monitor, for displaying information to the user, and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some aspects of the disclosed subject matter, a server transmits data (e.g., an HTML page) to a client device (e.g., for purposes of displaying data to and receiving user input from a user interacting with the client device). Data generated at the client device (e.g., a result of the user interaction) can be received from the client device at the server.

It is understood that any specific order or hierarchy of steps in the processes disclosed is an illustration of example approaches. Based upon design preferences, it is understood that the specific order or hierarchy of steps in the processes may be rearranged, or, in some cases, one or more of the illustrated steps may be omitted. Some of the steps may be performed simultaneously. For example, in certain circumstances, multitasking and parallel processing may be implemented. Moreover, the separation of various system components illustrated above should not be understood as requiring such separation, and it should be understood that the described program components and systems can generally be integrated together in a single software product or packaged into multiple software products.

Various modifications to these aspects will be readily apparent, and the generic principles defined herein may be applied to other aspects. Thus, the claims are not intended to be limited to the aspects shown herein, but are to be accorded the full scope consistent with the language claims, where reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject technology.

A phrase, for example, "an aspect," does not imply that the aspect is essential to the subject technology or that the aspect applies to all configurations of the subject technology. A disclosure relating to an aspect may apply to all configurations, or one or more configurations. A phrase, for example, "an aspect," may refer to one or more aspects and vice versa. A phrase, for example, "a configuration," does not imply that such configuration is essential to the subject technology or that such configuration applies to all configurations of the subject technology. A disclosure relating to a configuration may apply to all configurations, or one or more configurations. A phrase, for example, "a configuration," may refer to one or more configurations and vice versa.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the disclosed subject matter has been described with reference to specific example embodiments, various modifications and changes may be made to these embodiments without departing from the broader scope of embodiments of the present disclosure.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

In this document, the terms "a" or "an" are used, as is common in patent documents, to include one or more than one, independent of any other instances or usages of "at least one" or "one or more." In the appended claims, the terms "including" and "in which" are used as the plain-English equivalents of the respective terms "comprising" and "wherein." Also, in the following claims, the terms "including" and "comprising" are open-ended; that is, a system, device, article, or process that includes elements in addition to those listed after such a term in a claim are still deemed to fall within the scope of that claim. Moreover, in the following claims, the terms "first," "second," "third," and so forth are used merely as labels, and are not intended to impose numerical requirements on their objects.

What is claimed is:

1. A method comprising:
    accessing, at a computing machine, a product mention in a scientific or research-related text, the product mention including One or more attribute values for a plurality of attributes, each attribute being associated with either a single attribute value or no attribute value;
    determining that the attribute values of the product mention correspond to two or more candidate product matches in a product directory;
    identifying, at the computing machine and based at least in part on stored data related to the scientific or research-related text, a product match from among the candidate product matches, the product match corresponding to the product mention in the scientific or research-related text;
    providing an output of the product match for storage in conjunction with the product mention in the scientific or research-related text; and
    providing a graphical output for display in conjunction with the scientific or research-related text, the graphical output comprising a sidebar, the sidebar comprising a link to a page, the page including data representing at least a name of the product match, a manufacturer of the product match, and features of the product match, wherein the product mention is accessed at the computing machine based on training at a computer trained to identify a commercial product in a document by:
        receiving, at the computer, an input comprising plural documents with identified commercial products within the documents; and
        training the computer to compute a first score corresponding to whether the token corresponds to the commercial product using the input.

2. The method of claim 1, wherein identifying the product match from among the candidate product matches comprises:
    identifying one or more other scientific or research-related texts citing one or more of the candidate product matches and sharing one or more characteristics of the scientific or research-related text that includes the product mention;
    identifying, from among the candidate product matches, a subset corresponding to the candidate product matches cited in the one or more other scientific or research-related texts; and
    identifying the product match from the subset.

3. The method of claim 2, the characteristics comprising at least one of: one or more authors, an institutional affiliation of the one or more authors, a geographic region of the one or more authors, a time-frame of publication, and a topic of the scientific or research-related text.

4. The method of claim 1, wherein identifying the product match from among the candidate product matches comprises:
    identifying, from among the candidate product, matches and based on information stored in the product directory, a subset comprising candidate product matches sharing characteristics with the scientific or research-related text; and
    identifying the product match from the subset.

5. The method of claim 4, the characteristics comprising at least one of: availability at a time before a publication date of the scientific or research-related text and availability in a geographic region associated with an author of the scientific or research-related text.

6. The method of claim 1, wherein identifying the product match from among the candidate product matches comprises:
    providing, via a network, an output of at least a subset, of the candidate product matches; and
    receiving, via the network and in response to the output, an indication of the identified product match.

7. The method of claim 6, further comprising:
    computing, for each candidate product match, a second score representing a likelihood that the candidate product match is the product match; and
    arranging the two or more candidate product matches in an ordered list based on the second score,
    wherein the output includes the ordered list.

8. The method of claim 7, wherein the second score represents a probability that the candidate product match is the product match.

9. The method of claim 1, further comprising:
    determining that the attribute values of the product mention do not correspond to any candidate product matches in a product directory;
    providing, via a network, an output of a portion of the scientific or research-related text including the product mention; and
    receiving, via the network and in response to the output, an input comprising an addition to the product directory or a revision for an attribute value of the product mention, wherein determining that the attribute values of the product mention correspond to the two or more candidate product matches in the product directory is in response to the input.

10. The method of claim 1, wherein the plurality of attributes include: a name, a catalog identification number, a manufacturer, and a location of the manufacturer.

11. The method of claim 1, wherein the product directory comprises one or more product catalogs from one or more manufacturers.

12. A system comprising:
    one or more processors of a computing machine; and
    a memory comprising instructions which, when executed by the one or more processors, cause the computing machine to implement operations comprising:
        accessing, at a computing machine, a product mention in a scientific or research-related text, the product mention including one or more attribute values for a plurality of attributes, each attribute being associated with either a single attribute value or no attribute value;
        determining that the attribute values of the product mention correspond to two or more candidate product matches in a product directory;
        identifying, at the computing machine and based at least in part on stored data related to the scientific or research-related text, a product match from among the candidate product matches, the product match corresponding to the product mention in the scientific or research-related text;

providing an output of the product match for storage in conjunction with the product mention in the scientific or research-related text; and providing a graphical output for display in conjunction with the scientific or research-related text, the graphical output comprising a sidebar, the sidebar comprising a link to a page, the page including data representing at least a name of the product, match, a manufacturer of the product match, and features of the product match, wherein the product mention is accessed at, the computing machine based on training at, a computer trained to identify a commercial product in a document by:

receiving, at the computer, an input comprising plural documents with identified commercial products within the documents; and training the computer to compute a first score corresponding to whether the token corresponds to the commercial product using the input.

13. A non-transitory machine-readable medium comprising instructions which, when executed by a computing machine, cause the computing machine to implement operations comprising:

accessing, at the computing machine, a product mention in a scientific or research-related text, the product mention including one or more attribute values for a plurality of attributes, each attribute being associated with either a single attribute value or no attribute value;

determining that the attribute values of the product mention correspond to two or more candidate product matches in a product directory;

identifying, at the computing machine and based at least in part on stored data related to the scientific or research-related text, a product match from among the candidate product matches, the product match corresponding to the product mention in the scientific or research-related text;

providing an output of the product match for storage in conjunction with the product mention in the scientific or research-related text; and providing a graphical output for display in conjunction with the scientific or research-related text, the graphical output comprising a sidebar, the sidebar comprising a link to a page, the page including data representing at least a name of the product match, a manufacturer of the product match, and features of the product match, wherein the product mention is accessed at the computing machine based on training at a computer trained to identify a commercial product in a document by:

receiving, at the computer, an input comprising plural documents with identified commercial products within the documents; and training the computer to compute a first score corresponding to whether the token corresponds to the commercial product using the input.

14. The machine-readable medium of claim 13, wherein identifying the product match from among the candidate product matches comprises:

identifying one or more other scientific or research-related texts citing one or more of the candidate product matches and sharing one or more characteristics of the scientific or research-related text that includes the product mention;

identifying, from among the candidate product matches, a subset corresponding to the candidate product matches cited in the one or more other scientific or research-related texts; and identifying the product match from the subset.

15. The machine-readable medium of claim 14, the characteristics comprising at least one of:

one or more authors, an institutional affiliation of the one or more authors, a geographic region of the one or more authors, a time-frame of publication, and a topic of the scientific or research-related text.

16. The machine-readable medium of claim 13, wherein identifying the product match from among the candidate product matches comprises:

identifying, from among the candidate product matches and based on information stored in the product directory, a subset comprising candidate product matches sharing characteristics with the scientific or research-related text; and identifying the product match from the subset.

17. The machine-readable medium of claim 16, the characteristics comprising at least one of: availability at a time before a publication date of the scientific or research-related text and availability in a geographic region associated with an author of the scientific or research-related text.

18. The machine-readable medium of claim 13, wherein identifying the product match from among the candidate product matches comprises:

providing, via a network, an output of at least a subset of the candidate product matches; and receiving, via the network and in response to the output, an indication of the identified product match.

19. The machine-readable medium of claim 18, further comprising:

computing, for each candidate product match, a second score representing a likelihood that the candidate product match is the product match; and arranging the two or more candidate product matches in an ordered list based on the second score, wherein the output includes the ordered list.

20. The machine-readable medium of claim 13, further comprising:

determining that the attribute values of the product mention do not correspond to any candidate product matches in a product directory;

providing, via a network, an output of a portion of the scientific or research-related text including the product mention; and receiving, via the network and in response to the output, an input comprising an addition to the product directory or a revision for an attribute value of the product mention, wherein determining that the attribute values of the product mention correspond to the two or more candidate product matches in the product directory is in response to the input.

21. A method implemented at a computing machine comprising one or more processors and a memory, the method comprising:

accessing, at the computing machine, a product mention m a scientific or research-related text, the product mention including one or more attribute values for a plurality of attributes, each attribute being associated with either a single attribute value or no attribute value;

determining that the attribute values of the product mention do not correspond to any candidate product matches in a product directory;

providing, via a network, an output of a portion of the scientific or research-related text including the product mention;
receiving, via the network and in response to the output, an input comprising an addition to the product directory or a revision for an attribute value of the product mention;
determining that the attribute values of the product mention correspond to one product match in the product directory in response to the input; and
providing an output of the product match for storage in conjunction with the product mention in the scientific or research-related text, wherein the product mention is accessed at the computing machine based on training at a computer trained to identify a commercial product in a document by:
receiving, at the computer, an input comprising plural documents with identified commercial products within the documents; and
training the computer to compute a first score corresponding to whether the token corresponds to the commercial product using the input.

22. The method of claim 21, wherein the addition to the product directory comprises fixing an omission in the product directory.

23. The method of claim 21, wherein the addition to the product directory comprises correcting an entry in the product directory.

24. A system comprising:
one or more processors of a computing machine; and
a memory comprising instructions which, when executed by the one or more processors, cause the computing machine to implement operations comprising:
accessing, at the computing machine, a product mention in a scientific or research-related text, the product mention including one or more attribute values for a plurality of attributes, each attribute being associated with either a single attribute value or no attribute value;
determining that the attribute values of the product mention do not correspond to any candidate product matches in a product directory;
providing, via a network, an output of a portion of the scientific or research-related text including the product mention;
receiving, via the network and in response to the output, an input comprising an addition to the product directory or a revision for an attribute value of the product mention;
determining that the attribute values of the product mention correspond to one product match in the product directory in response to the input; and
providing an output of the product match for storage in conjunction with the product mention in the scientific or research-related text, wherein the product mention is accessed at the computing machine based on training at a computer trained to identify a commercial product in a document by:
receiving, at the computer, an input comprising plural documents identified commercial products within the documents; and
training the computer to compute a first score corresponding to whether the token corresponds to the commercial product using the input.

25. A non-transitory machine-readable medium comprising instructions which, when executed by a computing machine, cause the computing machine to implement operations comprising:
accessing, at the computing machine, a product mention in a scientific or research-related text, the product mention including one or more attribute values for a plurality of attributes, each attribute being associated with either a single attribute value or no attribute value;
determining that the attribute values of the product mention do not correspond to any candidate product matches in a product directory;
providing, via a network, an output of a portion of the scientific or research-related text including the product mention;
receiving, via the network and in response to the output, an input comprising an addition to the product directory or a revision for an attribute value of the product mention;
determining that the attribute values of the product mention correspond to one product match in the product directory in response to the input; and
providing an output of the product match for storage in conjunction with the product mention in the scientific or research-related text, wherein the product mention is accessed at the computing machine based on training at a computer trained to identify a commercial product in a document by:
receiving, at the computer, an input comprising plural documents with identified commercial products within the documents; and
training the computer to compute a first score corresponding to whether the token corresponds to the commercial product using the input.

* * * * *